United States Patent

Briscoe et al.

[11] Patent Number: 5,967,988
[45] Date of Patent: Oct. 19, 1999

[54] CATHETER HAVING ECHOGENICITY ENHANCEMENT

[75] Inventors: Roderick E. Briscoe, Rockford; Philip T. Goforth, Grand Rapids, both of Mich.

[73] Assignee: Medtronic, Inc., Minneapolis, Minn.

[21] Appl. No.: 09/057,321

[22] Filed: Apr. 8, 1998

[51] Int. Cl.⁶ .............................. A61B 8/12; A61M 25/10
[52] U.S. Cl. .............................. 600/458; 128/898; 604/96
[58] Field of Search .............................. 600/458; 604/437, 604/264, 272, 96–101; 128/898

[56] References Cited

U.S. PATENT DOCUMENTS

| | | |
|---|---|---|
| D. 302,589 | 8/1989 | McMenamy et al. . |
| 4,401,124 | 8/1983 | Guess et al. .............................. 600/458 |
| 4,428,379 | 1/1984 | Robbins et al. . |
| 4,582,061 | 4/1986 | Fry . |
| 4,869,259 | 9/1989 | Elkins . |
| 4,977,897 | 12/1990 | Hurwitz . |
| 5,081,997 | 1/1992 | Bosley, Jr. et al. .............................. 600/458 |
| 5,158,084 | 10/1992 | Ghiatas . |
| 5,490,521 | 2/1996 | Davis, Jr. et al. .............................. 600/458 |
| 5,759,154 | 6/1998 | Hoyns .............................. 600/458 |
| 5,766,151 | 6/1998 | Valley et al. .............................. 600/458 |

*Primary Examiner*—Francis J. Jaworski
*Attorney, Agent, or Firm*—Foley & Lardner

[57] ABSTRACT

An improved retrograde coronary sinus perfusion catheter includes a flexible, tubular catheter body and an inflatable balloon. The catheter body has proximal and distal ends and an interior lumen. The inflatable balloon is located adjacent the distal end of the catheter body and has proximal and distal edges. The improvement includes an echogenicity enhancement embedded within the catheter body. The echogenicity enhancement is adapted to reflect ultrasonic waves at a characteristic different from the catheter body.

31 Claims, 7 Drawing Sheets

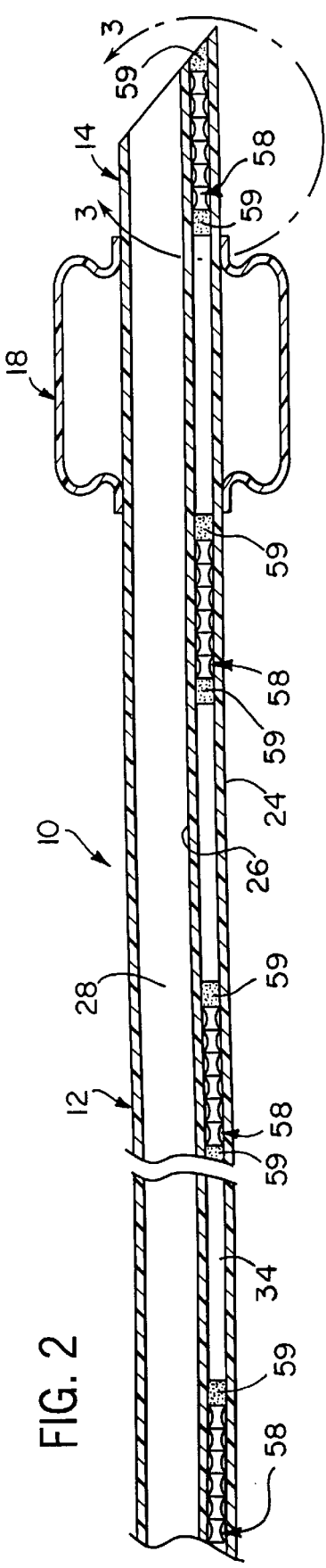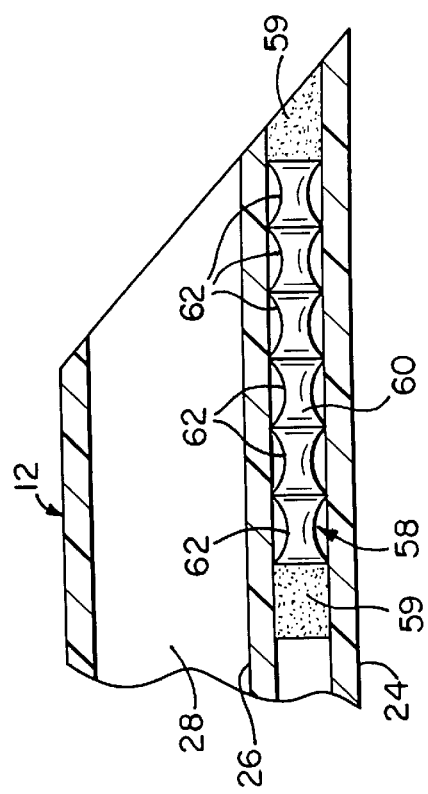

CATHETER HAVING ECHOGENICITY ENHANCEMENT

BACKGROUND OF THE INVENTION

1. Field of the Invention

The present invention relates to catheters. More particularly, the present invention relates to a cardioplegia catheter having an echogenicity enhancement to aid in detecting the position of the catheter within a body.

2. Description of the Related Art

Catheters have a wide variety of applications during surgical procedures. For example, in cardiac surgery, venous and arterial catheters are used to conduct blood between the body and bypass equipment. Catheters are used to conduct cardioplegic solutions for both antegrade and retrograde solution administration. Cardioplegic solutions, typically containing potassium, magnesium, procaine or a hypocalcemic solution, stop the heart by interfering with the heart's capacity to conduct the natural electric signals which cause beating of the heart. In normal antegrade cardioplegia, a single needle is inserted into the aorta, and cardioplegic solution is administered therethrough. The cardioplegic solution flows through the coronary arteries in the normal direction of blood flow. In retrograde cardioplegia, a balloon catheter is inserted into the coronary sinus. The balloon is then inflated, and the cardioplegic solution is perfused through the coronary veins in the opposite direction of blood flow.

Traditional cardiac surgery involves creating a large incision in the chest cavity to expose the heart. Under these surgical conditions proper placement of a catheter may be determined by either direct visual or sensory cues. However, a recent trend in surgical procedures is to minimize the size of access apertures formed in the chest cavity, thereby making it more difficult to confirm whether a catheter is properly positioned within the body and specifically within the aorta or coronary sinus. In these procedures, generally referred to as "Minimally Invasive Cardiac Surgery," the size of the aperture in the chest wall is reduced to a size slightly larger than that of the catheter to be inserted therein. As a result, other methods are needed to determine the location of the catheter within the body.

One way of confirming the location of a catheter within a body is with an ultrasonic pulse-echo imaging system. The term "echogenicity" refers to the relative extent that a surface reflects incident ultrasound wave energy directly back to a sensor, which is proximate the source or emitter of the ultrasonic wave energy. The low practical echogenicity of the prior art smooth catheters hampers accurate imaging of the catheter within the body. Typically, a needle or stylet of the catheter, or at least its point or tip, is echogenically enhanced to improve its ultrasound image, in order to more accurately pinpoint its placement during real-time ultrasonic guidance. Once the catheter is in place, the stylet is removed from the catheter. One disadvantage to this arrangement is that a needle or stylet is required in order to accurately determine the position of the catheter within the body. At times it may be desirable to use a catheter without a needle or stylet inserted therein.

There is a need, therefore, for an improved catheter having an echogenicity enhancement provided on the catheter itself. In addition, there is a need for an echogenically enhanced catheter that has smooth exterior and interior surfaces, so as not to interfere with insertion of the catheter into the body or with the transport of liquids therethrough.

SUMMARY OF THE INVENTION

The catheter according to the present invention overcomes the problems of the prior art by providing an echogenicity enhancement that is embedded within the body of the catheter. Thus, the present invention provides a catheter whose location within a vessel may be determined without the need for a stylet.

In accordance with one embodiment of the invention, an improved retrograde coronary sinus perfusion catheter includes a flexible, tubular catheter body and an inflatable balloon. The catheter body has proximal and distal ends and an interior lumen. The inflatable balloon is located adjacent the distal end of the catheter body and has proximal and distal edges. The improvement in the catheter includes an echogenicity enhancement embedded within the catheter body. The echogenicity enhancement is adapted to reflect ultrasonic waves at a characteristic different from the catheter body.

In accordance with another embodiment of the invention, a method for positioning a catheter in a vascular system of a body is provided. The method includes the step of providing a catheter including a catheter body and an echogenicity enhancement as described above. The method further includes the steps of inserting the distal end of the catheter into the vascular system and detecting the location of the catheter within the vascular system using an ultrasonic pulse-echo imaging system. The echogenicity enhancement reflects ultrasonic waves from the ultrasonic pulse-echo imaging system at a characteristic different from the catheter body. The catheter is then positioned at a specific location in the vascular system.

Other advantages of the invention will become apparent from the detailed description given hereinafter. It should be understood, however, that the detailed description and specific embodiments are given by way of illustration only, since, from this detailed description, various changes and modifications within the spirit and scope of the invention will become apparent to those skilled in the art.

BRIEF DESCRIPTION OF THE DRAWINGS

The invention will now be described with reference to the drawings in which:

FIG. 2 is a partial cross-sectional view of the catheter of FIG. 1, showing an echogenicity enhancement including a plurality of concave members;

FIG. 3 is partial cross-sectional view of the distal end of the catheter taken generally about the arc 3—3 of FIG. 2;

DETAILED DESCRIPTION OF THE PREFERRED EMBODIMENT

Figure 1:
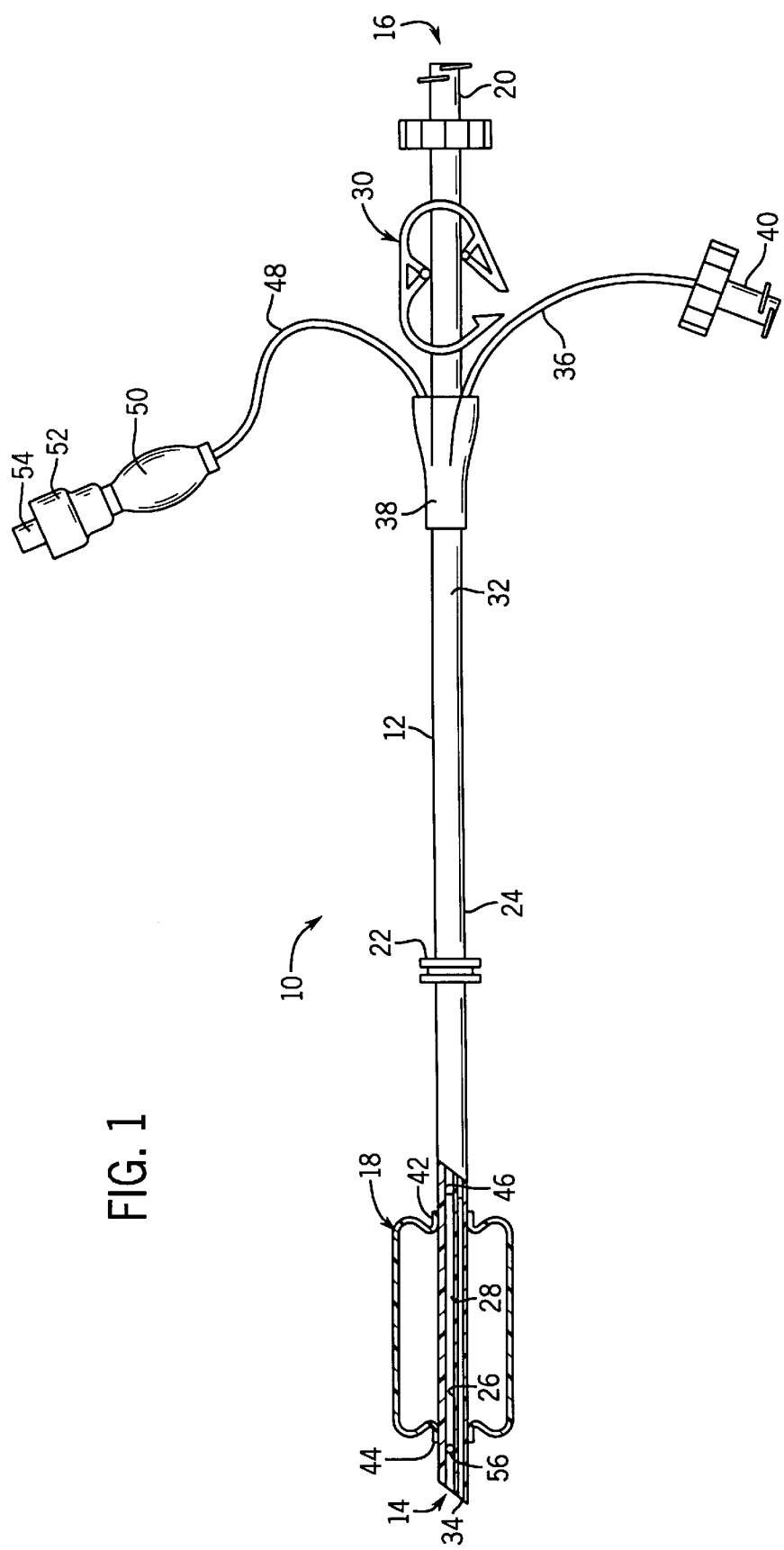
FIG. 1 is a side elevational view of a catheter according to the present invention.

Referring now to the drawings and to FIGS. 1-3 in particular, a preferred embodiment of a catheter 10 according to the invention is shown. The catheter 10, which may be used to introduce fluid to a body organ, includes a catheter body 12 having a distal end 14 and a proximal end 16. The catheter 10 further includes an inflatable balloon 18 coupled to the catheter body 12, proximate the distal end 14. Attached to the proximal end 16 of the catheter body 12 is a locking female luer 20. A suture ring 22, slidably mounted on the catheter body 12, serves as an aid for securing the catheter 10 in a human body.

The catheter body 12 is preferably formed of a flexible, plastic material, such as silicone, suitable for introduction into the human body. The catheter body 12 is generally tubular in cross section and has an outer surface 24 and an inner surface 26. The inner surface 26 defines an interior, infusion lumen 28. The conventional locking female luer 20 connects the catheter 10 to a source of cardioplegic solution (not shown). A clamping member 30 is mounted on the catheter body 12 adjacent to and distal of the locking female luer 20. The clamping member 30, which is of conventional design, selectively squeezes the catheter body 12 to occlude the interior, infusion lumen 28. In the preferred embodiment, the catheter body 12 further includes a coiled wire 32 incorporated therein, distal of the clamping member 30, to resist the collapse or kinking of the catheter body 12; however, this wire 32 is not a required element of the invention.

A separate pressure monitoring lumen 34, extending substantially along the length of the catheter body 12, provides pressure monitoring capability. The pressure monitoring lumen 34 is preferably integrally molded into the catheter body 12, except for its proximal end which exits near the proximal end 16 of the catheter body 12 to terminate into a pressure monitoring line 36. A strain relief sleeve 38, made of an elastic material, surrounds the catheter body 12 and the pressure monitoring line 36 at the point the pressure monitoring lumen 34 exits the catheter body 12. An adhesive may be used to help seal the sleeve 38 to the catheter body 12 and the pressure monitoring line 36.

Mounted on the proximal end of the pressure monitoring line 36 is a locking female luer 40 for connection to a pressure monitoring device (not shown). The locking female luer 40 may incorporate an integral three-way valve (not shown), so that the pressure monitoring line 36 may be simultaneously connected to alternatively selectable pressure monitoring devices. The pressure monitoring lumen 34 extends to the distal end 14 of the catheter body 12, thereby enabling the pressure monitoring device to be in fluid communication with the inside of the body organ in which the catheter 10 is inserted.

The inflatable balloon 18 is coupled to the outer surface 24 of the catheter body 12 proximate the distal end 14 and has a proximal edge 42 and a distal edge 44. A separate inflation lumen 46, which extends over substantially the entire length of the catheter body 12, provides a passageway for fluid used to inflate the balloon 18. The inflation lumen 46 is preferably integrally molded into the catheter body 12, except for its proximal end which exits the catheter body 12 at the strain relief sleeve 38 and which includes a separate, tubular inflation line 48. A conventional pilot balloon 50 and a one-way valve 52 with a female slip luer 54 are mounted on the proximal end of the inflation line 48.

The distal end of the inflation lumen 46 terminates inside of the balloon 18, so that fluid or air may pass through the inflation lumen 46 to fill the balloon 18. The one-way valve 52 prevents the fluid from escaping the balloon 18, and thus keeps the balloon 18 inflated until the one-way valve 52 is manually released, whereupon the fluid exits the balloon 18 through the inflation lumen 46 and past the open one-way valve 52.

At the distal end 14 of the catheter body 12, one or more auxiliary discharge apertures 56 may be provided. The auxiliary discharge apertures 56 are located distal of the inflation balloon 18 and lead from the interior of the inflation lumen 28 radially through the catheter body 12. If for some reason the distal end 14 of the catheter 10 were to become blocked or occluded in any manner, the auxiliary discharge apertures 56 would discharge the flow of cardioplegic solution into a coronary sinus.

As best illustrated in FIGS. 2 and 3, the catheter 10 includes a plurality of echogenicity enhancements 58 spaced at intervals along the length of the catheter body 12. The term "echogenicity" refers to the relative extent that a surface reflects incident ultrasound wave energy directly back to a sensor, which is proximal to the source or emitter of the ultrasonic wave energy. Ultrasound energy from a transducer (not shown) reflects off the echogenicity enhancements 58 and back to the transducer. Thus, the echogenicity enhancements 58 improve the ultrasonic image of the catheter 10 in order to determine with greater accuracy the location of the catheter 10 within the body.

The preferred embodiment of the invention includes a plurality of echogenicity enhancements 58 spaced along the length of the catheter. However, a single echogenicity enhancement 58 may be provided at the distal end 14 of the catheter body 12, or one or more echogenicity enhancements 58 may be provided at one or more edges of the inflatable balloon 18 to pinpoint the exact location of the balloon 18.

Each echogenicity enhancement 58 is preferably embedded within the catheter body 12 between the outer surface 24 and the inner surface 26, so as not to interfere with the insertion of the catheter 10 in a vascular system or with the flow of fluid through the interior, infusion lumen 28. As shown in FIGS. 2 and 3, the echogenicity enhancements 58 are located in the pressure monitoring lumen 34 and are secured in place by a silicone adhesive 59. Alternatively, the echogenicity enhancements 58 may be located in an auxiliary lumen (not shown) of the catheter body 12. Thus, the outer and inner surfaces 24 and 26 of the catheter body 12, respectively, remain smooth so as not to impede the insertion of the catheter 10 into the body or the flow of fluid through the infusion lumen 28. The echogenicity enhancements 58 are preferably made of metal, such as stainless steel or titanium dioxide. As shown in FIGS. 2 and 3, the echogenicity enhancements 58 include an elongate member 60 made up of a plurality of concave members 62.

Figure 4:
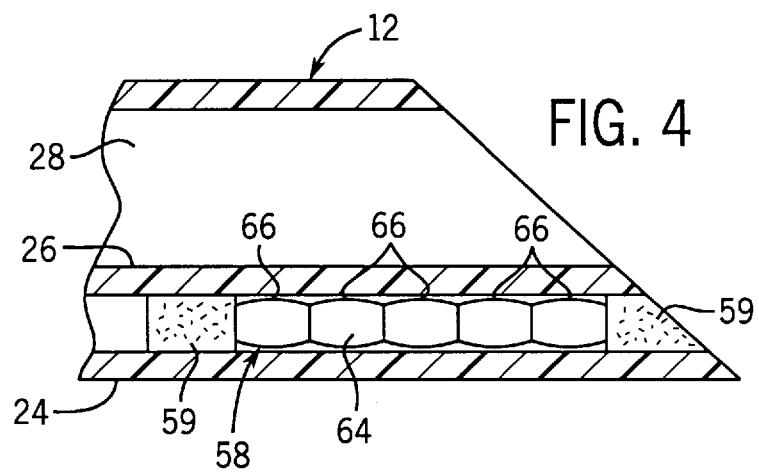
FIG. 4 is a partial sectional view of a second embodiment of a catheter according to the invention, wherein the echogenicity enhancement includes a plurality of convex members.
Figure 5:
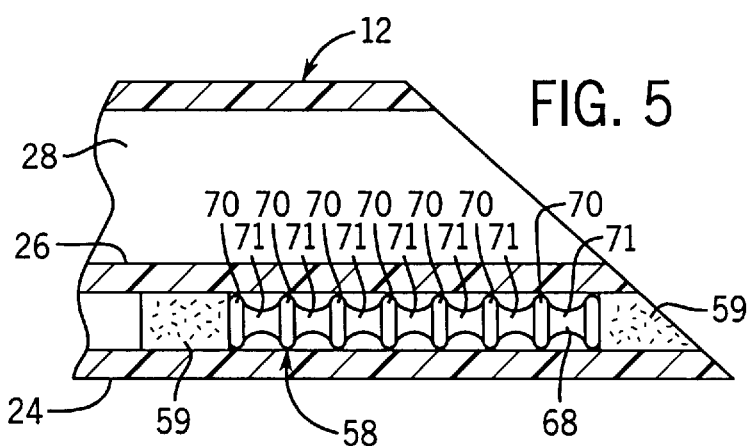
FIG. 5 is a partial sectional view of a third embodiment of a catheter according to the invention, wherein the echogenicity enhancement includes a series of alternating convex and concave members.
Figure 6:
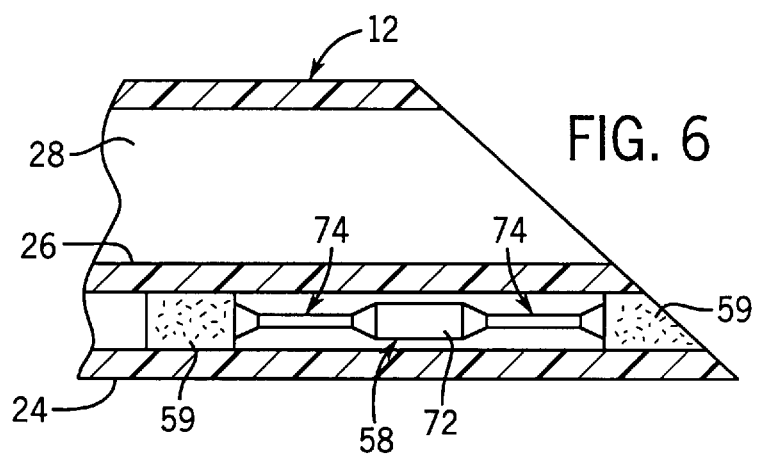
FIG. 6 is a partial sectional view of a fourth embodiment of a catheter according to the invention, wherein the echogenicity enhancement includes an elongate member having a plurality of equally spaced apart, truncated V-shaped, annular grooves.
Figure 7:
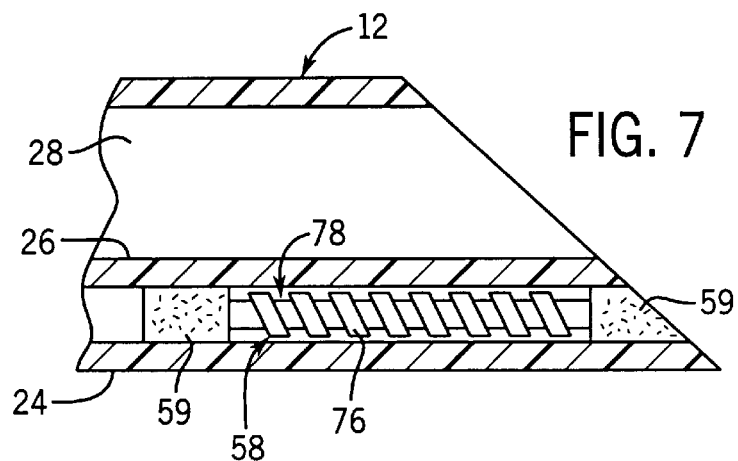
FIG. 7 is a partial sectional view of a fifth embodiment of a catheter according to the invention, wherein the echogenicity enhancement includes a continuous spiral member.

The elongate member 60 with the plurality of concave members 62 is only one way of improving the echogenicity of the catheter 10. Alternative echogenicity enhancements 58 are provided in FIGS. 4–13. As shown in FIG. 4, the echogenicity enhancement 58 includes an elongate member 64 having a plurality of convex members 66. The echogenicity enhancement 58 of the catheter 10 shown in FIG. 5 includes an elongate member 68 having a series of alternating convex members 70 and concave members 71. In FIG. 6, the echogenicity enhancement 58 includes an elongate member 72 with a plurality of equally spaced apart annular grooves 74, each groove 74 having a truncated V-shape. In the alternative, the grooves 74 may be formed as a continuous spiral, rather than separate annular grooves. For example, as shown in FIG. 7, the echogenicity enhancement 58 includes an elongate member 76 having a continuous spiral groove 78 formed therein. The groove 78 has a generally square cross-sectional shape.

Figure 8:
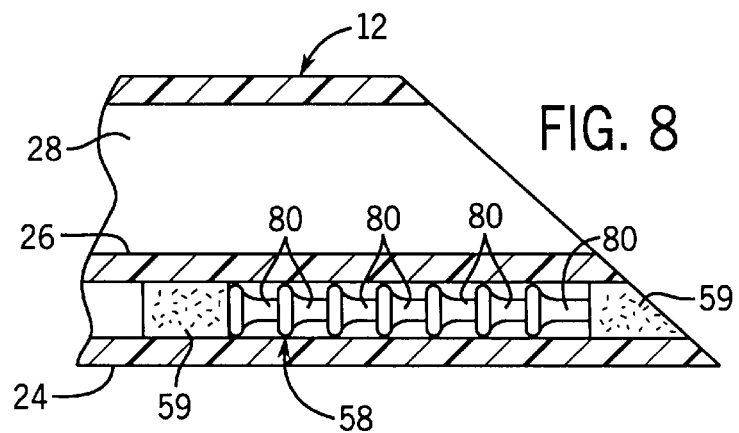
FIG. 8 is a partial sectional view of a sixth embodiment of a catheter according to the invention, wherein the echogenicity enhancement includes a plurality of conical, campanulate members arranged in end-to-end relationship.
Figure 9:
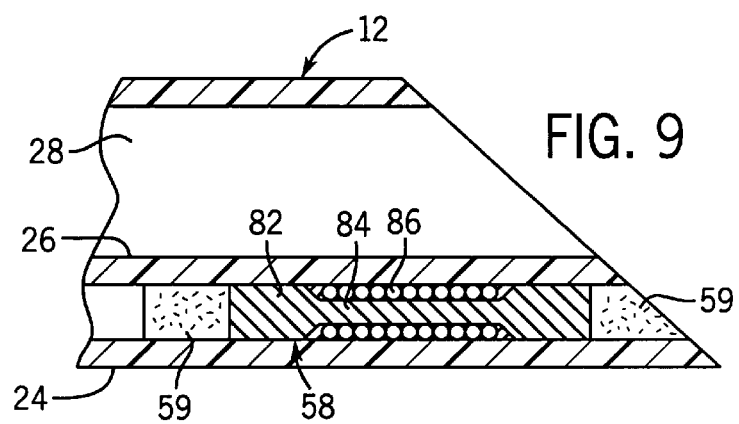
FIG. 9 is a partial sectional view of a seventh embodiment of a catheter according to the invention, wherein the echogenicity enhancement includes a wire coiled about an elongate member.
Figure 10:
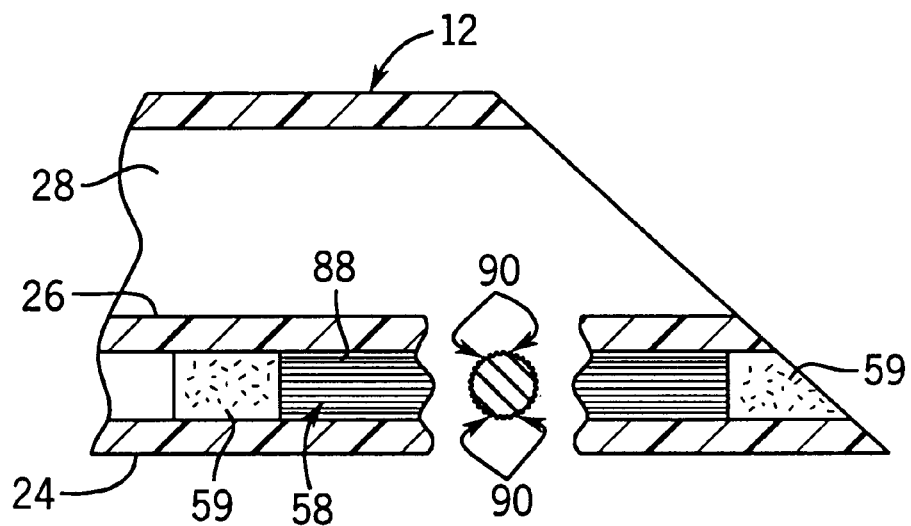
FIG. 10 is a partial sectional view of an eighth embodiment of a catheter according to the invention with a cut-away portion showing the cross section of the echogenicity enhancement, wherein the echogenicity enhancement includes an elongate member having a series of narrow and shallow longitudinal grooves.
Figure 11:
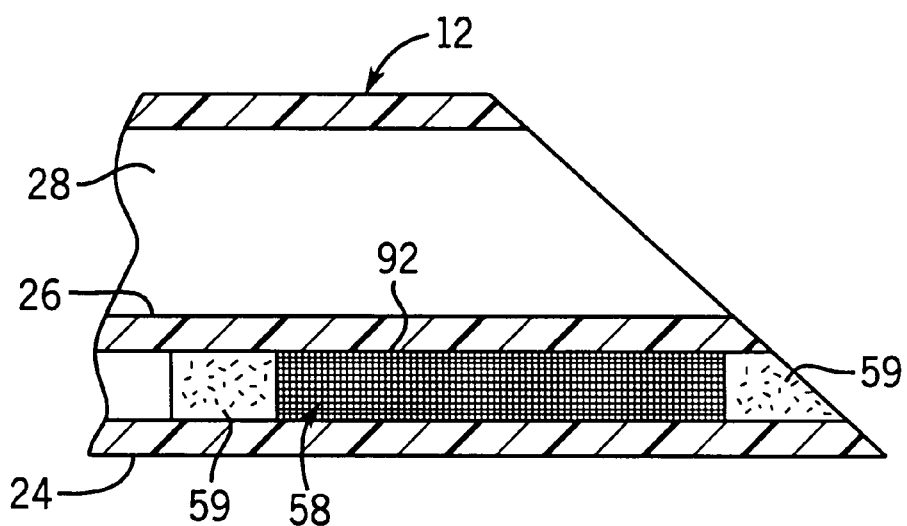
FIG. 11 is a partial sectional view of a ninth embodiment of a catheter according to the invention, wherein the echogenicity enhancement includes an elongate member having a cross-hatch pattern.
Figure 12:
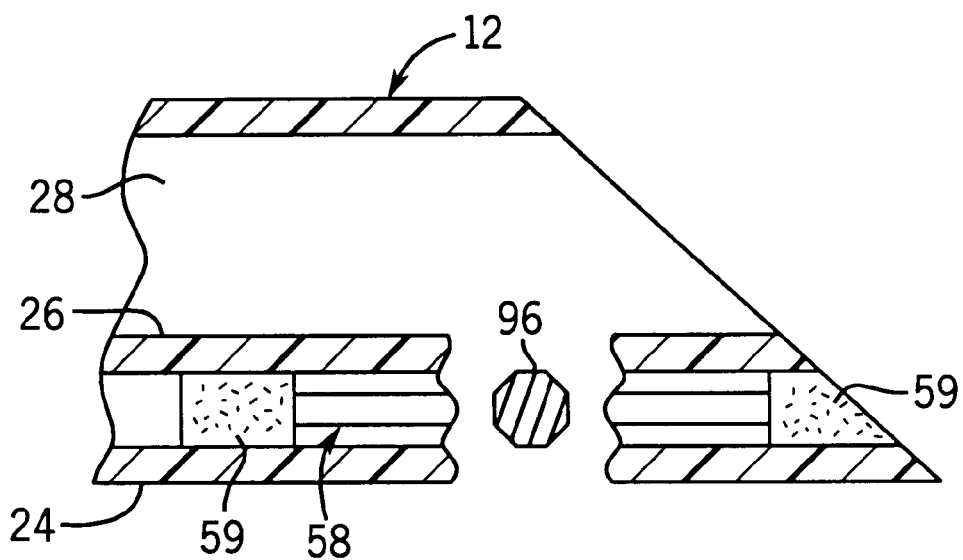
FIG. 12 is a partial sectional view of a tenth embodiment of a catheter according to the invention with a cut-away portion showing the cross section of the echogenicity enhancement, wherein the echogenicity enhancement includes an elongate member having a hexagonal cross-sectional shape.

As shown in FIG. 8, the echogenicity enhancement 58 includes a series of conical, campanulate members 80. The campanulate members 80 are arranged in end-to-end relationship. In FIG. 9 another echogenicity enhancement 58 includes an elongate member 84 having a reduced diameter portion 86. A coiled wire 88 spans the reduced diameter portion 86 of the elongate member 84. The ends of the coiled wire 88 are attached to the respective ends of the reduced diameter portion 86 of the elongate member 84. In the catheter 10 of FIG. 10, the echogenicity enhancement 58 includes an elongate member 88 having a series of narrow and shallow longitudinal grooves 90 formed in the surface thereof. Similarly, the echogenicity enhancement 58 of the catheter 10 shown in FIG. 11 is an elongate member 92 having a cross-hatched pattern 94 formed in a surface thereof. Alternative roughened sections similar to the cross-hatched pattern 94, such as a particle-blasted section (not shown), can also provide echogenicity enhancement.

Figure 13:
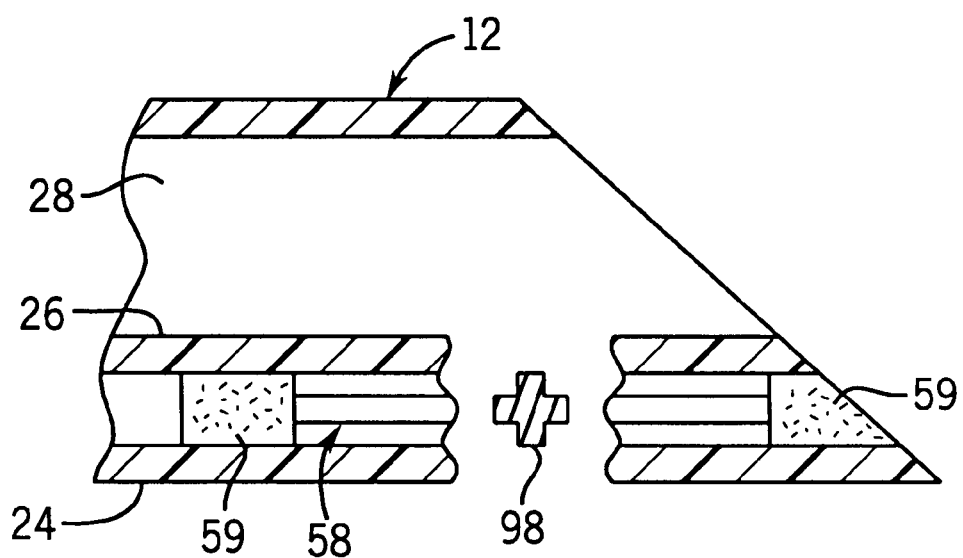
FIG. 13 is a partial sectional view of an eleventh embodiment of a catheter according to the invention with the cut-away portion showing the cross section of the echogenicity enhancement, wherein the echogenicity enhancement includes an elongate member having a cruciate cross-sectional shape.

In addition, the echogenicity enhancements 58 of the catheter 10 may include an elongate member having one of a variety of cross-sectional shapes. For example, FIG. 12, the echogenicity enhancement 58 may include an elongate member 96 having a hexagonal cross section (FIG. 13). In addition, FIG. 13 illustrates that the echogenicity enhancement 58 may be an elongate member 98 having a cruciate cross-sectional shape.

Catheters have a wide range of uses. For example, catheters may be inserted into the body through an aperture to access the urinary tract or the vascular system. The catheter 10 of the present invention may be adapted for any one of these uses. However, the catheter 10 is ideally suited for insertion into the vascular system and, more specifically, for retrograde or antegrade cardioplegia solution administration.

Figure 14:
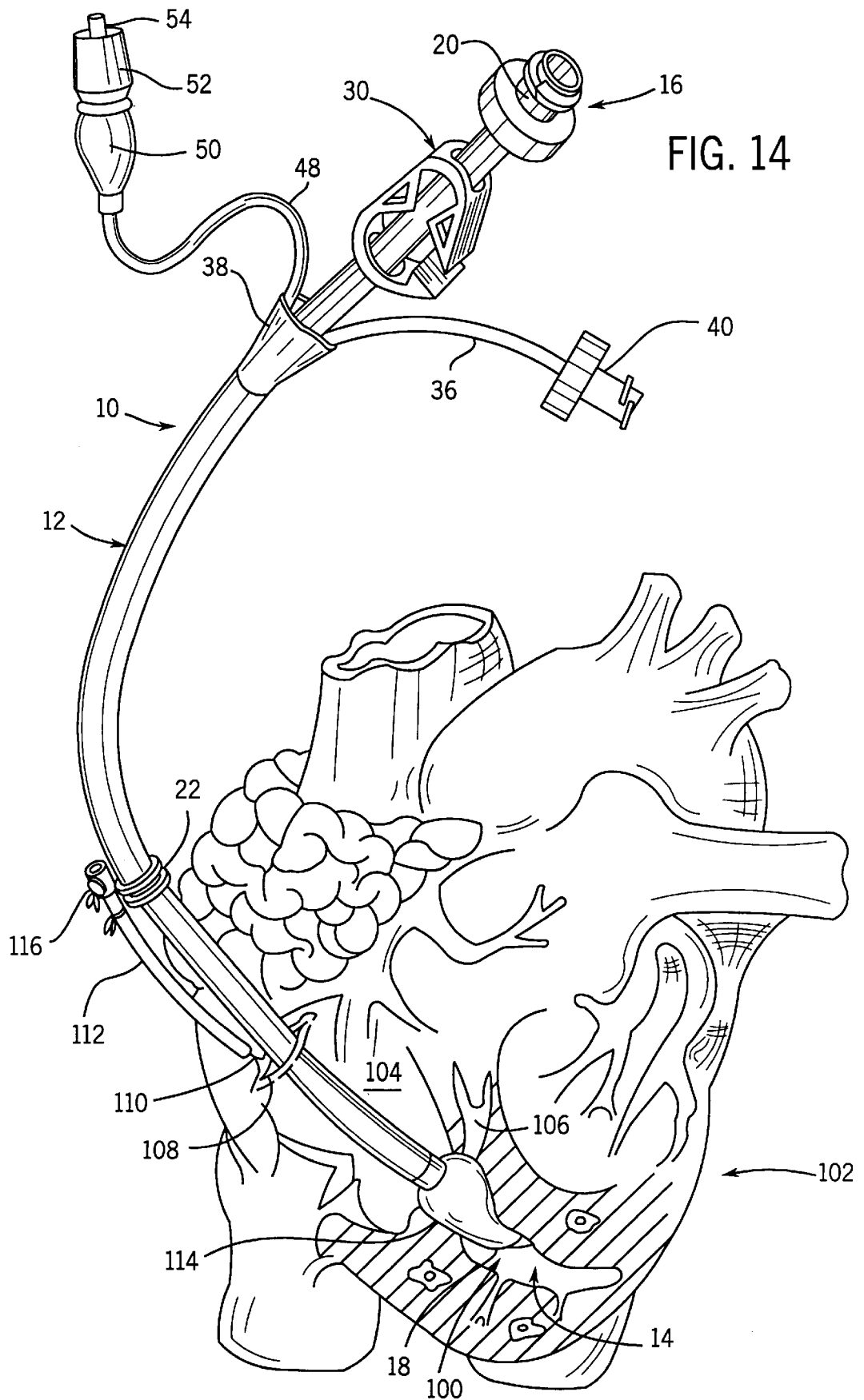
FIG. 14 is a partial sectional side elevational view of the catheter inserted into a coronary sinus vein.

By way of specific example, the catheter 10, as shown in FIG. 14, is positioned in the coronary sinus 100 of a heart 102. The coronary sinus 100 drains into the right atrium 104 of the heart 102. As illustrated in FIG. 14, the left coronary vein 106, one of the major blood vessels that drains a large area of the heart 102, enters the coronary sinus 10 immediately adjacent the ostium (opening) 114 of the coronary sinus 100 into the right atrium 104.

Some researchers believe that the open left coronary vein 106 allows cardioplegic solution, that is pumped into the coronary sinus 100, to bypass a portion of the circulatory system of the heart 102 and "leak" back into the coronary sinus 100 proximal of the inflatable balloon 18, through the left coronary vein 106. The cardioplegic solution that is pumped into the coronary sinus 100 will seek the path of least resistance. In this case, it is believed that the path of least resistance is not through the veins, into the capillaries and through the arteries to the aorta, but rather through a network of tiny vessels interconnecting the left coronary vein 106 and the coronary sinus 100. Thus, it is important that the catheter 10 be positioned in the heart 102 such that the inflatable balloon 18 blocks the junction between the left coronary vein 106 and the coronary sinus 100 to prevent cardioplegic solution from draining through the left coronary vein 106 back to the coronary sinus 100 adjacent the inflatable balloon 18. The placement of echogenicity enhancements 58 on the catheter body 12, particularly at the distal end 14 or at the proximal and distal edges 42 and 44, respectively, of the balloon 18, increases the accuracy with which the catheter 10 is positioned in the coronary sinus 100.

The catheter 10 is thus used in a surgical procedure as follows. First, the surgeon creates an atriotomy (an incision in the heart's atrium) 108 and a purse string suture 110 in the right atrial wall of the heart 102, leaving the free ends of the suture 110 extending through a tourniquet tube 112. The distal end 14 of the catheter 10 is introduced, through the atriotomy 108 and the purse string suture 110, into the right atrium 104 of the heart 102. The catheter body 12 is inserted into the coronary sinus 100 through its ostium 114. Using an ultrasonic pulse-echo imaging system (not shown), the surgeon advances the catheter 10 until it is properly positioned in the coronary sinus 100. The balloon 18 is then inflated to block the junction between the left coronary vein 106 and the coronary sinus 10. Once the catheter 10 is properly positioned, the purse string suture 110 is tightened, and a clamp 116 on the tourniquet tube 112 is closed to hold the ends of the suture 110. The pressure monitoring lumen luer 40 and the infusion lumen luer 20 are connected to their respective pressure monitor and cardioplegic sources, and the lumens are purged of air in the standard fashion. Suitable cardioplegic solution may then be introduced into the infusion lumen 28 through the proximal end 16 of the catheter 10 and conveyed to the heart 102. In the alternative, the catheter 10 may be inserted remotely through a jugular access (not shown). With this remote access, the surgeon would need to rely entirely on the image provided by the ultrasonic pulse-echo imaging system in order to position the cannula 10 within the body.

Reasonable variation and modification are possible within the spirit of the foregoing specification and drawings without departing from the scope of the invention.

What is claimed is:

1. An improved retrograde coronary sinus perfusion catheter including a flexible, tubular catheter body and an inflatable balloon, the catheter body having a proximal end, a distal end and an interior lumen, the inflatable balloon being located adjacent the distal end of the catheter body and having a proximal edge and a distal edge, the improvement comprising an echogenicity enhancement embedded within the catheter body, the echogenicity enhancement adapted to reflect ultrasonic waves at a characteristic different from the catheter body wherein the echogenicity enhancement is located in a secondary lumen proximate the distal end of the catheter body.

2. The improved retrograde coronary sinus perfusion catheter according to claim 1, wherein the echogenicity enhancement is embedded between an outer surface and an inner surface of the catheter body, the inner surface defining the interior lumen.

3. The improved retrograde coronary sinus perfusion catheter according to claim 1, wherein the echogenicity enhancement includes a plurality of concave members.

4. The improved retrograde coronary sinus perfusion catheter according to claim 1, wherein the echogenicity enhancement includes a plurality of convex members.

5. The improved retrograde coronary sinus perfusion catheter according to claim 1, wherein the echogenicity enhancement includes a series of alternating convex and concave members.

6. The improved retrograde coronary sinus perfusion catheter according to claim 1, wherein the echogenicity enhancement includes an elongate member.

7. The improved retrograde coronary sinus perfusion catheter according to claim 6, wherein the elongate member has a plurality of annular grooves formed therein, the plurality of annular grooves having truncated V-shape.

8. The improved retrograde coronary sinus perfusion catheter according to claim 6, wherein the elongate member has a continuous spiral groove formed therein.

9. The improved retrograde coronary sinus perfusion catheter according to claim 6, wherein the elongate member has a reduced diameter portion and a coiled wire disposed about the reduced diameter portion.

10. The improved retrograde coronary sinus perfusion catheter according to claim 6, wherein the elongate member has a plurality of longitudinal grooves formed therein.

11. The improved retrograde coronary sinus perfusion catheter according to claim 6, wherein the elongate member has a cross-hatch pattern.

12. The improved retrograde coronary sinus perfusion catheter according to claim 6, wherein the elongate member has a hexagonal cross-sectional shape.

13. The improved retrograde coronary sinus perfusion catheter according to claim 6, wherein the elongate member has a cruciate cross-sectional shape.

14. The improved retrograde coronary sinus perfusion catheter according to claim 1, wherein the echogenicity enhancement includes a plurality of campanulate members.

15. The improved retrograde coronary sinus perfusion catheter according to claim 1, wherein the echogenicity enhancement is located proximate at least one of the proximal and distal edges of the inflatable balloon.

16. The improved retrograde coronary sinus perfusion catheter according to claim 1, wherein a plurality of echogenicity enhancements are located at spaced intervals along the catheter body.

17. The improved retrograde coronary sinus perfusion catheter according to claim 1, wherein the echogenicity enhancement includes a radiopaque material.

18. The improved retrograde coronary sinus perfusion catheter according to claim 17, wherein the radiopaque material includes stainless steel.

19. The improved retrograde coronary sinus perfusion catheter according to claim 1, wherein the echogenicity enhancement is secured to the catheter body by an adhesive.

20. The improved retrograde coronary sinus perfusion catheter according to claim 19, wherein the adhesive is a silicone adhesive.

21. A method for positioning a cardioplegia catheter in a vascular system of a body, the method comprising the steps of:
   providing a cardioplegia catheter including a catheter body having a proximal end, a distal end and an interior lumen, the catheter further including an echogenicity enhancement located between an outer surface and an inner surface of the lumen proximate the distal end of the catheter body, the inner surface defining the interior of the lumen, the echogenicity enhancement being located within a secondary lumen, and the catheter including an inflatable balloon;
   inserting the distal end of the catheter into the coronary sinus;
   detecting the location of the catheter within the vascular system using an ultrasonic pulse-echo imaging system, the echogenicity enhancement reflecting ultrasonic waves from the ultrasonic pulse-echo imaging system at a characteristic different from the catheter body; and
   positioning the inflatable balloon in a sinus ostium to seal the coronary sinus.

22. The method for positioning a catheter according to claim 21, wherein the inflatable balloon has a proximal edge and a distal edge, and the echogenicity enhancement is located proximate at least one of the proximal and distal edges.

23. The method for positioning a catheter according to claim 21, wherein the echogenicity enhancement includes a plurality of concave members.

24. The method for positioning a catheter according to claim 21, wherein the echogenicity enhancement includes a plurality of convex members.

25. The method for positioning a catheter according to claim 21, wherein the echogenicity enhancement includes an elongate member having a groove formed therein.

26. The method for positioning a catheter according to claim 25, wherein the elongate member has a plurality of annular grooves, the plurality of annular grooves having a truncated V-shape.

27. The method for positioning a catheter according to claim 25, wherein the groove is a continuous spiral groove.

28. The method for positioning a catheter according to claim 25, wherein the elongate member has a plurality of longitudinal grooves.

29. The method for positioning a catheter according to claim 21, wherein the echogenicity enhancement includes a plurality of campanulate members.

30. The method for positioning a catheter according to claim 21, wherein a plurality of echogenicity enhancements are located at spaced intervals along the catheter body.

31. The method for positioning a catheter according to claim 21, wherein the echogenicity enhancement includes a radiopaque material.

* * * * *